(12) United States Patent
Allen et al.

(10) Patent No.: US 6,583,274 B1
(45) Date of Patent: Jun. 24, 2003

(54) CRYSTALLINE FORMS OF MACROLIDE ANTIBIOTIC

(75) Inventors: Douglas J. M. Allen, New London, CT (US); Barry J. Morton, Gales Ferry, CT (US); Robert J. Rafka, Stonington, CT (US); Colman B. Ragan, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/563,792

(22) Filed: May 2, 2000

Related U.S. Application Data

(60) Provisional application No. 60/134,644, filed on May 18, 1999.

(51) Int. Cl.[7] .......................... C07H 17/08; C07H 1/00; A01N 43/04
(52) U.S. Cl. .......................... 536/7.2; 536/7.4; 536/124; 514/29
(58) Field of Search .......................... 536/7.2, 7.4, 124; 514/29

(56) References Cited

U.S. PATENT DOCUMENTS

| 5,441,939 A | * 8/1995 | Yang .......................... 514/29 |
| 5,844,105 A | * 12/1998 | Liu et al. ................... 536/18.5 |
| 6,268,489 B1 | * 7/2001 | Allen et al. ................... 536/7.4 |

FOREIGN PATENT DOCUMENTS

| WO | 9856802 | 12/1998 | |
| WO | WO 98/56802 | * 12/1998 | ........... C07H/17/08 |

OTHER PUBLICATIONS

Wilkening et al.('Novel Transannular Rearrangements of Azalide Iminoethers, Tetrahedron vol. 53, No. 50, pp. 16923–16944, 1997).*

* cited by examiner

*Primary Examiner*—Jeffrey Siew
(74) *Attorney, Agent, or Firm*—Peter C. Richardson; Gregg C. Benson; B. Timothy Creagan

(57) ABSTRACT

Novel crystalline forms of a compound of Formula 1 are disclosed:

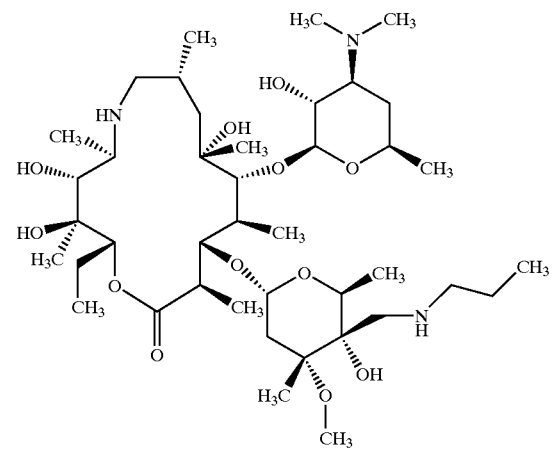

Also disclosed are pharmaceutical compositions comprising these forms, and methods of their preparation and use.

20 Claims, 8 Drawing Sheets

CRYSTALLINE FORMS OF MACROLIDE ANTIBIOTIC

This application claims benefit to U.S. Provisional application Ser. No. 60/134,644, filed May 18, 1999.

FIELD OF THE INVENTION

This invention relates to novel crystalline forms of a macrolide antibiotic, compositions comprising them, and methods of their preparation and use.

BACKGROUND OF THE INVENTION

The macrolide referred to herein as CP-472,295 has the structure shown in Formula 1:

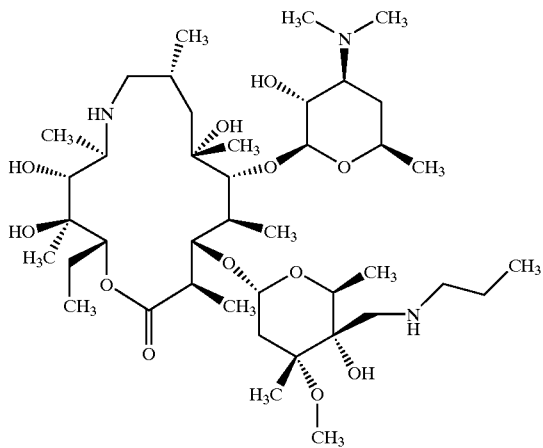

CP-472,295 possesses antibiotic properties, and is useful in the treatment of, for example, bacterial and protozoal infections. As with all drugs, the safe and effective use of CP-472,295 depends on the ability of those skilled in the art to accurately administer it in precise amounts.

The accurate delivery of precise amounts of a drug is facilitated by the preparation of dosage forms. It is well known, however, that the ease with which dosage forms are prepared depends on factors such as, but not limited to, the solubility, homogeneity, hygroscopicity, and flow characteristics of the drug. Often, these properties are improved if crystalline, rather than amorphous, forms of the drug can be produced. There thus exists a need for well characterized, crystalline forms of CP-472,295. A particular need exists for non-hygroscopic forms of CP-472,295.

SUMMARY OF THE INVENTION

This invention is directed to crystalline forms of CP-472,295, to pharmaceutical compositions comprising these crystalline forms, and to methods of their preparation and use.

A first embodiment of the invention thus encompasses crystalline forms of a compound of Formula 1.

A preferred crystalline form of the compound of Formula 1 is anhydrous.

A preferred crystalline form of the compound of Formula I has an X-ray powder diffraction pattern which exhibits characteristic peaks expressed in 2θ at about 6.0, 8.6, 9.7, 15.4, 15.9, 17.5, 18.2, 18.7, and 21.

A preferred crystalline form of the compound of Formula 1 has a differential scanning calorimetry spectrum comprising an event with an onset at about 193° C.

A preferred crystalline form of the compound of Formula 1 is non-hygroscopic for about 72 hours when stored at about 87% relative humidity and 25° C.

A preferred crystalline form of the compound of Formula 1 is a monohydrate.

A preferred crystalline form of the compound of Formula 1 has an X-ray powder diffraction pattern that exhibits characteristic peaks expressed in 2θ at about 6.2, 7.6, 9.2, 9.5, 12.3, 12.9, 14.2, 4.6, 17.8, and 19.5.

A preferred crystalline form of the compound of Formula 1 has single crystal parameters which are substantially the same as those provided in Table 1:

TABLE 1

| Crystal Parameters | |
|---|---|
| Unit Cell Dimensions | a = 10.557(1) Å |
| | b = 19.396(1) Å |
| | c = 23.223(1) Å |
| | α = 90.00° |
| | β = 90.0° |
| | Y = 90.0° |
| | V = 4755.26(6) Å$^3$ |
| Space Group | P2$_1$2$_1$2$_1$ |
| Molecules per Unit Cell | 4 |
| Density (g/cm) | 1.151 |

A particularly preferred crystalline form of the compound of Formula 1 comprises atoms at atomic positions relative to the origin of the unit cell as set forth below in Table 2, bond lengths as set forth below in Table 3, or bond angles as set forth in Table 4.

A preferred crystalline form of the compound of Formula 1 has a differential scanning calorimetry spectrum comprising an event with an onset at about 75° C.

A preferred crystalline form of the compound of Formula 1 is non-hygroscopic for about 7 days when stored at about 87% relative humidity and 25° C.

A preferred crystalline form of the compound of Formula 1 is a sesquahydrate.

A preferred crystalline form of the compound of Formula 1 has an X-ray powder diffraction pattern that exhibits characteristic peaks expressed in 2θ at about 5.2, 7.4, 11.2, 11.7, 12.3, 12.9, 14.9, 15.4, 16.7, and 17.9.

A preferred crystalline form of the compound of Formula 1 has a differential scanning calorimetry spectrum comprising an event with an onset at about 101° C.

A second embodiment of the invention encompasses pharmaceutical compositions comprising a crystalline form of a compound of Formula 1 and a pharmaceutically acceptable carrier. The crystalline form of the compound of Formula 1 can be anhydrous, a monohydrate, or a sesquahydrate. The pharmaceutical compositions of the invention are suitable for oral, rectal, parental (intravenous, intramuscular), transdermal, buccal, nasal, sublingual, or subcutaneous administration.

A third embodiment of the invention encompasses processes of preparing crystalline forms of a compound of Formula 1.

A preferred process is a process of preparing a crystalline anhydrous form of a compound of Formula 1 which comprises: dissolving an amount of a compound of Formula 1 in an anhydrous, low polarity solvent; cooling the solution to a temperature at which the full amount of the compound of Formula 1 is no longer soluble in the solution; and isolating by filtration any crystals that are formed. The invention encompasses products of this process.

A preferred process is a process of preparing a crystalline monohydrate form of a compound of Formula 1 which comprises: dissolving an amount of a compound of Formula 1 in a non-aqueous solvent containing between about 0.05 and about 15 percent by volume water; cooling the solution to a temperature at which the full amount of the compound of Formula 1 is no longer soluble in the solution; and isolating by filtration any crystals that are formed. The invention encompasses products of this process.

A preferred process is a process of preparing a crystalline sesquahydrate form of a compound of Formula 1 which comprises: dissolving an amount of a compound of Formula 1 in ethyl acetate containing between about 1 and about 10 percent by volume water; cooling the solution to a temperature at which the full amount of the compound of Formula 1 is no longer soluble in the solution; and isolating by filtration any crystals that are formed. The invention encompasses products of this process.

A fourth embodiment of the invention encompasses a method of treating a bacterial or protozoal infection in a mammal comprising administering to a mammal in need of such treatment a therapeutically effective amount of a crystalline form of a compound of Formula 1. The crystalline form of the compound of Formula 1 can be anhydrous, a monohydrate, or a sesquahydrate.

Definitions

Figure 1:
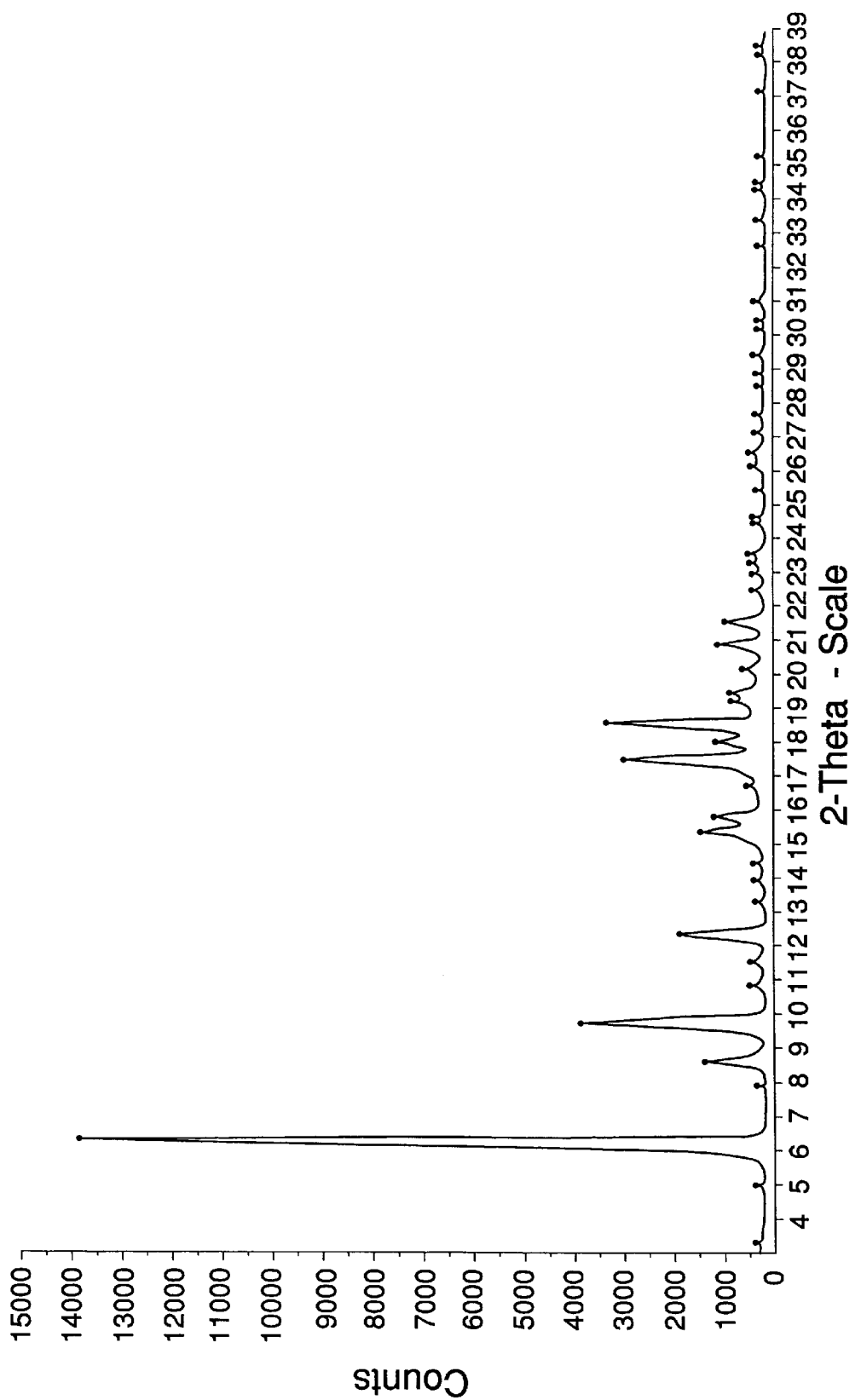
FIG. 1: X-ray powder diffraction pattern of crystalline anhydrous CP-472,295. Vertical axis is intensity (CPS); horizontal axis is two theta (degrees).

As used herein, the term "non-hygroscopic" when used to describe a composition of matter means that the composition of matter absorbs moisture at a rate of less than about 0.4% over 24 hours at 90% relative humidity.

As used herein, the term "mammal" encompasses human, dog, and cat.

As used herein the terms "bacterial infection(s)" and "protozoal infection(s)" include bacterial infections and protozoal infections that occur in mammals, fish and birds as well as disorders related to bacterial infections and protozoal infections that may be treated or prevented by antibiotics such as the compounds of the invention. Such bacterial infections and protozoal infections, and disorders related to such infections, include the following: pneumonia, otitis media, sinusitis, bronchitis, tonsillitis and mastoiditis related to infection by Staphylococcus pneumoniae, Haemophilus influenzae, Moraxella catarrhalis, Staphlococcus aureus, or Peptostreptococcus spp.; pharynigis, rheumatic fever and glomerulonephritis related to infection by Streptococcus pyogenes, Groups C and G streptococci, Clostridium diptheriae, or Actinobacillus haemolyticum; respiratory tract infections related to infection by Mycoplasma pneumoniae, Legionella pneumophila, Streptococcus pneumoniae, Haemophilus influenzae, or Chlamydia pneumoniae; uncomplicated skin and soft tissue infections, abscesses and osteomyelitis, and puerperal fever related to infection by Staphlococcus aureus, coagulase-positive staphlococci (i.e., S. epidermis., S. hemolyticus, etc.), Staphylococcus pyogenes, Streptococcus agalactiae, Streptococcal groups C-F (minute-colony streptococci), viridans streptococci, Corynebacterium minutissimum, Clostridium spp., or Bartonella henselae; uncomplicated acute urinary tract infections related to infection by Staphylococcus saprophyticus or Enterococcus spp.; urethritis and cervicitis; and sexually transmitted diseases related to infection by Chlamydia trachomatis, Haemophilus ducreyi, Treponema pallidum, Ureaplasma urealyticum, or Neiserria gonorrhea; toxin diseases related to infection by S. aureus (food poisoning and Toxic Shock Syndrome), or Groups A, B and C streptococci; ulcers related to infection by Helicobacterpylort, systemic febrile syndromes related to infection by Borrelia recurrentis; Lyme disease related to infection by Borrelia burgdorferi, conjunctivitis, keratitis, and dacrocystitis related to infection by Chlamydia trachomatis, Neisseria gonorrhoeae, S. aureus, S. pneumoniae, S. pyogenes, H. influenzae, or Listeria spp.; disseminated Mycobacterium avium complex (MAC) disease related to infection by Mycobacterium avium, or Mycobacterium intracellulare; gastroenteritis related to infection by Campylobacter jejuni, intestinal protozoa related to infection by Cryptosporidium spp.; odontogenic infection related to infection by viridans streptococci; persistent cough related to infection by Bordetella pertussis; gas gangrene related to infection by Clostridium perfringens or Bacteroides spp.; and atherosclerosis related to infection by Helicobacter pylori or Chlamydia pneumoniae. Bacterial infections and protozoal infections and disorders related to such infections that may be treated or prevented in animals include the following: bovine respiratory disease related to infection by P. haem., P. multocida, Mycoplasma bovis, or Bordetella spp.; cow enteric disease related to infection by E coli or protozoa (i.e., coccidia, cryptosporidia, etc.); dairy cow mastitis related to infection by Staph. aureus, Strep. uberis, Strep. agalactiae, Strep. dysgalactiae, Klebsiella spp., Corynebacterium, or Enterococcus spp.; swine respiratory disease related to infection by A. pleuro., P. multocida or Mycoplasma spp.; swine enteric disease related to infection by E coli Lawsonia intracellularis, Salmonella, or Serpulina hyodyisinteriae; cow footrot related to infection by Fusobacterium spp.; cow metritis related to infection by E coli; cow hairy warts related to infection by Fusobacterium necrophorum or Bacteroides nodosus; cow pink-eye related to infection by Moraxella bovis; cow premature abortion related to infection by protozoa (i.e., neosporium) urinary tract infection in dogs and cats related to infection by E co/~, skin and soft tissue infections in dogs and cats related to infection by Staph. epidermidis, Staph. intermedius, coagulase neg. Staph. or P. multocida; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections and disorders related to such infections that may be treated or prevented in accord with the methods of the invention are referred to in Sanford, J. P., et aL, "The Sanford Guide To Antimicrobial Therapy," 27 th Edition (Antimicrobial Therapy, Inc., 1996).

DETAILED DESCRIPTION OF THE INVENTION

This invention is based upon the discovery of three distinct polymorphs (i.e., crystalline structures) of CP-472, 295. These polymorphs possess unexpected physical properties which facilitate the manufacture of dosage forms of the compound.

A preferred polymorph of the compound is the crystalline anhydrous form. This form has an acicular (needle-like) habit with moderate birefringence. Parallel twinning can cause the crystals to appear as laths, and hampers the isolation of single crystals suitable for single crystal X-ray measurement. Graph 1 above shows a characteristic X-ray powder diffraction pattern of the crystalline anhydrous form.

Graph 2 above shows a characteristic differential scanning calorimetry (DSC) thermogram of the crystalline anhydrous form. Only a single event, which has an onset at about 193° C., is observed. Fusion microscopy of this form of CP-472, 295 reveals no events other than the melt.

A particular advantage conferred by this form is its lack of hygroscopicity. The following Graph 7 shows a characteristic hygroscopic measurement of the form:

From this and other data, it has been determined that crystalline anhydrous CP-472,295 is non-hygroscopic at about 87% relative humidity for about 72 hours at ambient temperature. This unexpected property allows the low-cost, efficient handling and storage of the drug, and the facile incorporation of accurate amounts of the drug into a variety of dosage forms.

Like the anhydrous form, the crystalline CP-472,295 monohydrate is also unexpectedly nonhygroscopic. This form appears in plate or equant habit, which may be the result of plate stacking and agglomeration. Graph 3 shows a characteristic X-ray powder diffraction pattern of this form. Crystals suitable for single crystal X-ray analysis can be obtained; data obtained from such analysis provides the representation of the crystalline structure shown above.

Graph 4 shows a characteristic DSC thermogram of crystalline CP-472,295 monohydrate. DSC and fusion microscopy show that this form begins to lose water and converts to a pseudomorph from about 70° C. to about 75° C. This pseudomorph can also be formed by placing the crystalline monohydrate under vacuum at ambient temperature. When not under vacuum, the pseudomorph melts at about 165° C., and then rapidly converts to the crystalline anhydrous form which, as above, melts at about 193° C.

Crystalline CP-472,295 monohydrate, like the crystalline anhydrous form described above, is advantageously non-hygroscopic. Graph 4 shows a characteristic hygroscopic measurement of the form. From this and other data, it has been determined that crystalline CP-472,295 monohydrate is non-hygroscopic at about 87% relative humidity for about 7 days at ambient temperature. This unexpected property allows the low-cost, efficient handling and storage of the drug, and the facile incorporation of accurate amounts of the drug into a variety of dosage forms.

By contrast, the pseudomorph formed when the monohydrate loses water is hygroscopic, and reabsorbs the water of hydration within about 4 hours when stored at about 87% relative humidity at ambient temperature.

The crystalline sesquahydrate form of CP-472,295 possesses different physical properties than the two forms described above. This form appears in a lath habit with moderate birefringence. Graph 5 shows a characteristic X-ray powder diffraction pattern of this form.

Unlike the monohydrate, this form of CP-472,295 readily loses water under routine handling conditions (e.g., 25° C. and 70% relative humidity). Graph 6 shows a characteristic DSC thermogram of crystalline CP-472,295 sesquahydrate. DSC and fusion microscopy show water loss at about 35° C., followed by crystallization to the anhydrous form which, as above, melts at about 193° C.

Each of the three crystalline compositions of matter disclosed herein may be prepared from amorphous (i.e., non-crystalline) or impure CP-472,295. The synthesis of CP-472,295 is disclosed by WO 98/56802, which is incorporated herein by reference.

A preferred method of forming crystalline anhydrous CP-472,295 comprises dissolving the amorphous compound in a dry solvent or solvent mixture. Preferred solvents include heptane, acetone, and acetonitrile. Other solvents, such as ethanol, isopropanol, and tetrahydrofuran may be used, but tend to produce mixtures of anhydrous, monohydrate, and sesquahydrate products. Preferably, the solvent is heated, the amorphous compound dissolved in it to a point approximately equal to saturation, and the resulting solution allowed to cool to a temperature at which the full amount of the compound dissolved is no longer soluble in the solvent. Crystals are isolated by filtration and air dried.

The crystalline anhydrous form can also be made by diffusion crystallization. For example, one or more miscible solvents in which CP-472,295 is poorly soluble are added to a solution into which amorphous CP-472,295 has been dissolved.

Another method of forming crystalline anhydrous CP-472,295 comprises dehydration of the crystalline monohydrate form of the compound. This can be done using heat, optionally under reduced pressure.

Crystalline CP-472,295 monohydrate can be isolated from a solvent or solvent mixture which contains some water, preferably from about 0.05 to about 15 percent water by volume, more preferably from about 1 to about 10 percent water by volume. With the exception of ethyl acetate, the isolation of this form does not appear to be affected by the polarity of the solvent. A preferred method of isolating the monohydrate comprises heating a solvent mixture such as ethanol/10% water or isopropyl ether/1% water, dissolving amorphous CP-472,295 in the mixture such that saturation or near saturation is obtained, and then cooling the mixture to a temperature at which the full amount of the compound dissolved is no longer soluble in the solvent mixture. Crystals are isolated by filtration and air dried.

Crystalline CP-472,295 sesquahydrate can also be isolated from wet solvents using conventional crystallization methods. It is preferred, however, that it be formed by dissolving amorphous CP-472,295 in heated ethyl acetate containing from about 1 to about 10 percent water by volume, more preferably from about 2 to about 6 percent water by volume, and cooling the resulting mixture to a temperature at which the full amount of the compound dissolved is no longer soluble in the solvent. Crystals are isolated by filtration.

Pharmaceutical Formulations and Methods of Treatment

The compounds of this invention (i.e., crystalline anhydrous CP-472,295, crystalline CP-472,295 monohydrate, and crystalline CP-472,295 sesquahydrate; hereinafter also referred to as "the active compounds") can be administered by oral, rectal, parenteral (i.e., intravenous, intramuscular), transdermal, buccal, nasal, sublingual, and subcutaneous routes. In general, the active compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight, and condition of the subject being treated and the particular route of administration chosen. A dosage level that is in the range of about 1 mg/kg/day to about 100 mg/kg/day is preferred, and a dosage level of macrolide antibiotic that is in the range of about 2 mg/kg/day to about 50 mg/kg/day is most preferred. Variations may nevertheless occur depending upon the species being treated (e.g., a human suffering from a bacterial or protozoal infection) and its individual response to the macrolide antibiotic, as well as on the type of pharmaceutical formulation chosen and the time period and interval at which such administration is carried out. In some instances, dosage levels below the lower limit of the aforesaid ranges may be more than adequate, while in other cases still larger doses may be employed without causing any harmful side effects provided that such larger doses are first divided into several small doses for administration throughout the day.

The active compounds may be administered alone or in combination with pharmaceutically acceptable carriers or diluents by the routes previously indicated. Such administration may be carried out in single or multiple doses. The active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents; or fillers, sterile aqueous media and various non-toxic organic solvents. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinyl pyrrol idone, sucrose, gelatin and acacia. Lubricating agents, surfactants, and glidants such as magnesium stearate, sodium lauryl sulfate, and talc are also useful for tableting purposes. Solid compositions of a similar type may also be employed as fillers in gelatin capsules. Preferred fillers include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with diluents such as water, ethanol, propylene glycol, glycerin and various like combinations thereof.

In addition to the common dosage forms set out above, the compounds of the invention may be administered by controlled release means and/or delivery devices capable of releasing the active compound at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. Suitable controlled release pharmaceutical compositions and delivery devices that may be adapted for the administration of the active compounds of the invention are described by U.S. Pat. Nos.: 3,847,770; 3,916,899; 3,536,809; 3,598,123; 3,630,200; 4,008,719; 4,687,610; 4,769,027; 5,674,533; 5,059,595; 5,591,767; 5,120,548 5,073,543; 5,639,476; 5,354,566; and 5,733,566, the disclosures of which are hereby incorporated by reference. For example, the active compounds may be coupled to a class of biodegradable polymers useful in achieving controlled release of a drug, for example, polylactic acid, polyglycolic acid, copolymers of polylactic and polyglycolic acid, polyepsion caprolatone, polyhydroxy butyric acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

For parenteral administration, solutions of an active compound in either sesame or peanut oil or in aqueous propylene glycol may be employed. The aqueous solutions should be suitably buffered if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds of the invention topically. This may be done by way of creams, jellies, gels, pastes, patches, ointments and the like, in accordance with standard pharmaceutical practice. The active compounds may further be administered in the feed of animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinlpyrrolidone, pyran copolymer, polyhydroxypropylmethacrylamide phenyl, polyhydroxyethylaspartamide-phenol, or polyethyleneoxide-polylysine substituted with palmitoyl residues.

Additional novel and non-limiting aspects of the compositions of matter of the invention are provided by the Examples.

EXAMPLES

Example 1

Preparation of Crystalline AnhVdrous CP-472,295

Approximately 20 mg of amorphous CP-472,295, prepared according to the method of WO 98/56802, were placed in pre-scratched 1 dram vials. Crystallization was attempted using diethyl ether, acetonitrile, acetone, methyl isobutyl ketone (MIBK), tert-butyl methyl ether (MTBE), and benzene.

The amorphous compound in each vial was forced into solution by adding small, heated quantities of each solvent. The vials were set aside to cool to room temperature; and formation of crystals (white needles) was observed in the acetone, acetonitrile, and MIBK systems.

Crystals were also obtained using diffusion crystallization wherein diethyl ether was the diffusing solvent, and ethyl acetate, ethanol, acetonitrile, n-propanol, and MIBK were used as base solvents. Crystal growth was observed for the ethanol/diethyl ether system.

Example 2

Preparation of Crystalline CP-472,295 Monohydrate

A water-saturated diethyl ether solution (0.9% water by volume) was formed by shaking diethyl ether against water. The aqueous layer was removed, and the organic layer filtered to provide a clear solution to which was added CP-472,295 until saturation was obtained. When kept at room temperature, the crystalline monohydrate precipitated from the solution within about 1 minute.

The crystalline monohydrate form was also formed by dissolving amorphous CP-472,295 in 2 ml of water-saturated MTBE until saturation was reached, and then decanting the solution. Precipitation of the compound occurred after the decanted solution sat at room temperature for approximately 15 minutes.

Example 3

Single Crystal Structure of Crystalline CP-472,295 Monohydrate

A representative crystal obtained using the method of Example 2 (diethyl ether) was surveyed and a 1 A data set was collected on a Siemens R3RA/v diffractometer. Atomic scattering factors were taken from the international Tables for X-ray Crystallography, Vol. IV, pp. 55, 99, 149, (Birmingham: Kynoch Press, 1974). All crystallographic calculations were facilitated by the SHELXTL system. See, Sheldrick, G. M., SHELXTL, *User Manual, Nicolet Instrument Co.,* 1981. All diffractometer data was collected at room temperature.

A trial structure, which was obtained by direct methods, refined routinely. A difference map revealed a water of crystallization. Hydrogen positions were calculated wherever possible. The methyl hydrogens and the hydrogens on nitrogen and oxygen were located by difference Fourier techniques. The hydrogen parameters were added to the structure factor calculations but were not refined. The shifts calculated in the final cycle of least squares refinement were all less than 0.1 of their corresponding standard deviations, and the final R index was 6.29%. A final difference Fourier revealed no missing or misplaced electron density.

Details of the crystal are provided by Table 1 above. Selected atomic coordinates and isotropic thermal parameters determined from the data are provided in Table 2.

TABLE 2

Atomic Coordinates (×10) and Isotropic Thermal Parameters (Axi 03) of CP-472,295 Monohydrate

| Atom | x | y | z | U |
| --- | --- | --- | --- | --- |
| O(1) | 5018(3) | 5945 | 7383(2) | 54(1) |
| C(2) | 6028(4) | 5657(3) | 7336(3) | 48(1) |
| C(3) | 6207(4) | 4909(3) | 7462(3) | 38(1) |
| C(4) | 7653(3) | 4785(3) | 7299(3) | 37(1) |
| C(5) | 7779(4) | 4493(3) | 6693(3) | 38(1) |
| C(6) | 9169(4) | 4552(3) | 6488(3) | 40(1) |
| C(7) | 9473(4) | 5214(3) | 6143(3) | 43(1) |
| C(8) | 8867(4) | 5199(3) | 5533(3) | 53(1) |
| C(9) | 9018(4) | 5840(3) | 5153(3) | 56(1) |
| C(10) | 7862(4) | 6306(3) | 5163(3) | 65(1) |
| N(11) | 7626(4) | 6592(3) | 5752(3) | 58(1) |
| C(12) | 6355(4) | 6834(3) | 5878(3) | 62(1) |
| C(13) | 6206(4) | 6810(3) | 6530(3) | 56(1) |
| C(14) | 4850(4) | 6951(3) | 6783(3) | 65(1) |
| C(15) | 4855(4) | 6702(3) | 7412(3) | 57(I) |
| O(16) | 6722(3) | 5972(3) | 7961(2) | 72(1) |
| C(17) | 5690(4) | 4443(3) | 7941(3) | 51(1) |
| O(18) | 8252(3) | 4328(2) | 7703(2) | 35(1) |
| C(19) | 8710(4) | 4657(3) | 8205(3) | 40(1) |
| O(20) | 9792(3) | 5060(2) | 8098(2) | 50(1) |
| C(21) | 10918(4) | 4662(3) | 7972(3) | 50(1) |
| C(22) | 11306(4) | 4210(3) | 8482(3) | 52(1) |
| C(23) | 10160(4) | 3726(3) | 8628(3) | 54(1) |
| C(24) | 8940(4) | 4147(3) | 8677(3) | 44(1) |
| C(25) | 11894(4) | 5207(3) | 7790(3) | 63(1) |
| O(26) | 12354(3) | 3795(3) | 8296(2) | 68(1) |
| C(26A) | 11874(4) | 4605(3) | 8987(3) | 77(1) |
| N(26B) | 11031(4) | 5067(3) | 9292(3) | 83(1) |
| C(26C) | 11775(4) | 5397(4) | 9731(3) | 141(1) |
| C(26D) | 11128(4) | 5662(3) | 10254(3) | 139(1) |
| C(26E) | 10157(4) | 5184(3) | 10518(3) | 111(1) |
| C(27) | 10373(4) | 3322(3) | 9184(3) | 76(1) |
| O(28) | 10149(3) | 3265(2) | 8140(2) | 54(1) |
| C(28A) | 9134(4) | 2782(3) | 8089(3) | 75(1) |
| C(29) | 7248(4) | 3748(3) | 6662(3) | 49(1) |
| O(30) | 9525(3) | 3988(2) | 6110(2) | 46(1) |
| C(31) | 10221(4) | 3448(3) | 6344(3) | 47(1) |
| O(32) | 11465(3) | 3717(2) | 6464(2) | 43(1) |
| C(33) | 12290(4) | 3201(3) | 6706(3) | 46(1) |
| C(34) | 12517(4) | 2638(3) | 6246(3) | 55(1) |
| C(35) | 11236(4) | 2339(3) | 6062(3) | 42(1) |
| C(36) | 10313(4) | 2892(3) | 5889(3) | 51(1) |
| C(37) | 13499(4) | 3556(3) | 6870(3) | 59(1) |
| N(38) | 11254(4) | 1800(3) | 5606(3) | 60(1) |
| C(39) | 11779(4) | 1156(3) | 5816(3) | 78(1) |
| C(40) | 11874(4) | 2009(3) | 5072(3) | 79(1) |
| O(41) | 9105(3) | 2605(3) | 5813(3) | 77(1) |
| C(42) | 10909(4) | 5304(3) | 6094(3) | 66(1) |
| C(43) | 9284(4) | 5634(3) | 4531(3) | 68(1) |
| C(45) | 6057(4) | 7527(3) | 5597(3) | 74(1) |
| O(46) | 7068(3) | 7282(3) | 6783(2) | 68(1) |
| O(47) | 4657(4) | 7681(2) | 6786(3) | 80(1) |
| C(48) | 3797(4) | 6626(30 | 6434(3) | 69(1) |
| C(49) | 3668(4) | 6856(3) | 7762(3) | 69(1) |
| O(51) | 8999(3) | 5783(2) | 6477(2) | 54(1) |
| C(52) | 3794(4) | 6731(3) | 8391(3) | 85(1) |
| O(1W) | 8868(4) | 6632(3) | 7432(2) | 83(1) |

Selected bond lengths determined from the single crystal data are provided in Table 3.

TABLE 3

Bond Lengths of CP-472,295 Monohydrate

| O(I)-C(2) | 1.340(6) | O(1)-C(15) | 1.480(6) |
| --- | --- | --- | --- |
| C(2)-C(3) | 1.517(8) | C(2)-O(16) | 1.217(7) |
| C(3)-C(4) | 1.591(6) | C(3)-C(17) | 1.533(8) |
| C(4)-C(5) | 1.522(8) | C(4)-O(18) | 1.438(7) |
| C(5)-C(6) | 1.547(6) | C(5)-C(29) | 1.552(8) |
| C(6)-C(7) | 1.549(8) | C(6)-C(30) | 1.450(7) |
| C(7)-C(8) | 1.554(8) | C(7)-C(42) | 1.530(6) |

TABLE 3-continued

Bond Lengths of CP-472,295 Monohydrate

| | | | |
|---|---|---|---|
| C(7)-O(51) | 1.438(7) | C(8)-C(9) | 1.532(9) |
| C(9)-C(10) | 1.519(7) | C(9)-C(43) | 1.525(9) |
| C(10)-N(11) | 1.499(9) | N(I1)-C(12) | 1.450(6) |
| C(12)-C(13) | 1.523(9) | C(I2)-C(45) | 1.529(9) |
| C(I3)-C(14) | 1.571(7) | C(I3)-O(46) | 1.418(7) |
| C(I4)-C(15) | 1.539(10) | C(14)-O(47) | 1.431(8) |
| C(14)-C(48) | 1.513(8) | C(15)-C(49) | 1.524(7) |
| O(18)-C(19) | 1.413(7) | C(19)-O(20) | 1.405(6) |
| C(19)-C(24) | 1.498(8) | O(20)-C(21) | 1.446(6) |
| C(2I)-C(22) | 1.528(9) | C(21)-C(25) | 1.535(8) |
| C(22)-C(23) | 1.568(7) | C(22)-0(26) | 1.434(6) |
| C(22)-C(26A) | 1.525(9) | C(23)-C(24) | 1.530(7) |
| C(23)-C(27) | 1.528(9) | C(23)-O(28) | 1.444(8) |
| C(26A)-N(26B) | 1.448(8) | N(26B)-C(26C) | 1.437(8) |
| C(26C)-C(26D) | 1.485(9) | C(26D)-C(26E) | 1.512(8) |
| O(28)-C(28A) | 1.428(7) | O(30)-C(31) | 1.391(7) |
| C(3I)-O(32) | 1.441(6) | C(31)-C(36) | 1.512(9) |
| O(32)-C(33) | 1.441(7) | C(33)-C(34) | 1.547(9) |
| C(33)-C(37) | 1.499(7) | C(34)-C(35) | 1.532(6) |
| C(35)-C(36) | 1.503(7) | C(35)-N(38) | 1.489(8) |
| C(36)-O(41) | 1.403(6) | N(38)-C(39) | 1.450(8) |
| N(38)-C(40) | 1.461(8) | C(49)-C(52) | 1.486(10) |

TABLE 4

Bond Angles of CP-472,295 Monohydrate

| | | | |
|---|---|---|---|
| C(2)-O(1)-C(15) | 119.1(4) | (I)-C(2)-C(3) | 112.4(4) |
| 0(3)-C(2)-0(16) | 122.7(5) | C(3)-C(2)O(16) | 124.8(5) |
| C(2)-C(3)-C(4) | 109.2(4) | C(2)-C(3)-C(I7) | 109.1(5) |
| C(4)-C(3)-C(17) | 115.2(4) | C(3)-C(4)-C(5) | 111.2(4) |
| C(3)-C(4)-O(18) | 111.1(4) | C(5)-C(4)-O(18) | 109.7(4) |
| C(4)-C(5)-C(6) | 109.9(4) | C(4)-C(5)-C(29) | 110.9(5) |
| C(6)-C(5)-C(29) | 113.3(4) | C(5)-C(6)-C(7) | 114.6(4) |
| C(5)-C(6)-O(30) | 112.3(4) | C(7)-C(6)-O(30) | 105.0(5) |
| C(6)-C(7)-C(8) | 111.7(4) | C(6)-C(7)-C(42) | 109.7(4) |
| C(8)-C(7)-C(42) | 110.1(5) | C(6)-C(7)-O(51) | 106.6(4) |
| C(8)-C(7)-O(51) | 111.3(4) | C(42)-C(7)-O(51) | 107.3(4) |
| C(7)-C(8)-C(9) | 117.8(5) | C(8)-C(9)-C(10) | 113.0(4) |
| C(8)-C(9)-C(43) | 110.7(5) | C(10)-C(9)-C(43) | 108.5(5) |
| C(9)-C(10)-N(11) | 111.6(5) | C(10)-N(11)-C(12) | 117.3(5) |
| N(11)-C(12)-C(13) | 106.6(4) | N(11)-C(12)-C(45) | 112.9(5) |
| C(13)-C(12)-C(45) | 115.4(5) | C(12)-C(13)-C(14) | 117.4(4) |
| C(12)-C(13)-0(46) | 109.1(5) | C(14)-C(13)-O(46) | 108.5(5) |
| C(13)-C(14)-C(15) | 107.3(4) | C(13)-C(14)-O(47) | 107.7(4) |
| C(15)-C(14)-0(47) | 107.8(5) | C(13)-C(14)-C(48) | 113.4(5) |
| C(15)-C(14)-C(48) | 112.3(5) | O(47)-C(14)-C(48) | 108.1(4) |
| O(1)-C(I5)-C(14) | 105.6(5) | O(1)-C(15)-C(49) | 108.3(4) |
| O(14)-C(15)-C(49) | 116.3(4) | C(4)-O(18)-C(19) | 114.3(4) |
| O(18)-C(19)-O(20) | 112.6(5) | O(18)-C(19)-C(24) | 111.2(5) |
| O(20)-C(I9)-C(24) | 111.4(4) | C(19)-O(20)-C(21) | 114.0(4) |
| O(20)-C(21)-C(22) | 111.8(5) | C(20)-C(21)-C(25) | 103.9(4) |
| C(22)-C(21)-C(25) | 115.3(4) | C(2I)-C(22)-C(23) | 107.7(4) |
| C(21)-C(22)-0(26) | 107.3(5) | C(23)-C(22)-0(26) | 108.9(5) |
| C(21)-C(22)-C(26A) | 114.4(5) | C(23)-C(22)-C(26A) | 115.9(5) |
| 0(26)-C(22)-C(26A) | 102.1(4) | C(22)-C(23)-C(24) | 110.2(5) |
| C(22)-C(23)-C(27) | 112.294) | C(24)-C(23)-C(27) | 109.5(5) |
| C(22)-C923)0(28) | 101.9(4) | C(24)-C(23)-O(28) | 112.5(4) |
| C(27)-C(23)-O(28) | 110.4(5) | C(19)-C(24)-C(23) | 115.7(5) |
| C(22)-C(26A)-N(26B) | 116.5(4) | C(26A)-N(26B)-C(26C) | 106.6(4) |
| N(26B)-C(26C)-C(26D) | 118.8(4) | C(26C)-C(26D)-C(26E) | 115.6(6) |
| C(23)-O(28)-C(28A) | 118.5(4) | C(6)-O(30)-C(31) | 118.0(5) |
| O(30)-C(31)-O(32) | 106.5(4) | O(30)-C(31)-C(36) | 107.5(5) |
| O(32)-C(3I)-C(36) | 109.6(4) | C(3I)-O(32)-C(33) | 112.0(4) |
| O(32)-C(33)-C(34) | 108.3(5) | O(32)-C(33)-C(37) | 107.2(5) |
| C(34)-C(33)-C(37) | 111.6(4) | C(33)-C(34)-C(35) | 108.9(4) |
| C(34)-C(35)-C(36) | 112.2(5) | C(34)-C(35)-N(38) | 116.9(4) |
| C(36)-C(35)-N(38) | 108.7(5) | C(31)-C(36)-C(35) | 111.3(5) |
| C(31)-C(36)-O(41) | 108.2(4) | C(35)-C(36)-O(41) | 109.9(5) |
| C(35)-N(38)-C(39) | 111.8(5) | C(35)-N(38)-C(40) | 114.5(4) |
| C(39)-N(38)-C(40) | 110.7(5) | C(15)-C(49)-C(52) | 114.8(4) |

The above three dimensional structure shows a plot of the refined crystal structure. The absolute configuration was not determined in this analysis because no "heavy atom" was present in the structure.

Example 4

Preparation of Crystalline CP-472,295 Sesquahydrate

CP-472,295 (0.3 grams) was dissolved in 1 ml ethyl acetate at room temperature. To the clear solution was added 0.4 ml water. The solution was stirred overnight, during which time the sesquahydrate formed as a precipitate. The precipitate was removed by filtration.

This invention is not to be limited by the examples and details provided above, and its scope is further defined by the claims appended hereto.

What is claimed is:

1. A crystalline form of a compound of Formula 1:

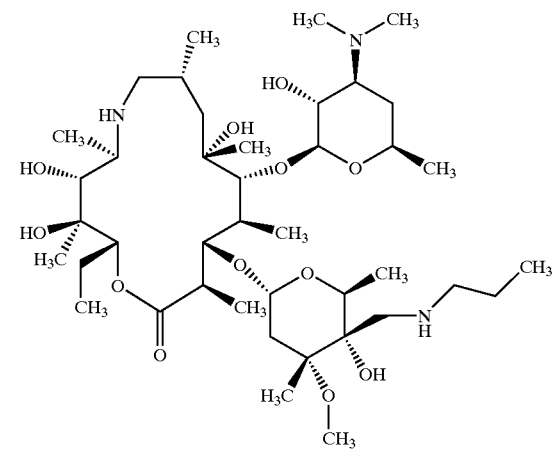

Formula 1

2. A crystalline form of claim 1 wherein said crystalline form is one of anhydrous, monohydrate and sesquahydrate.

3. A crystalline form of claim 1 which has an X-ray powder diffraction pattern that exhibits characteristic peaks expressed in 2θ at about 6.0, 8.6, 9.7, 15.4, 15.9, 17.5, 18.2., 18.7., and 21.

4. The crystalline form of claim 3 which has an X-ray powder diffraction pattern according to FIG. 1.

5. A crystalline form of claim 1 which has a differential scanning calorimetry spectrum comprising an event with an onset at about 75° C. or about 193° C.

Figure 2:
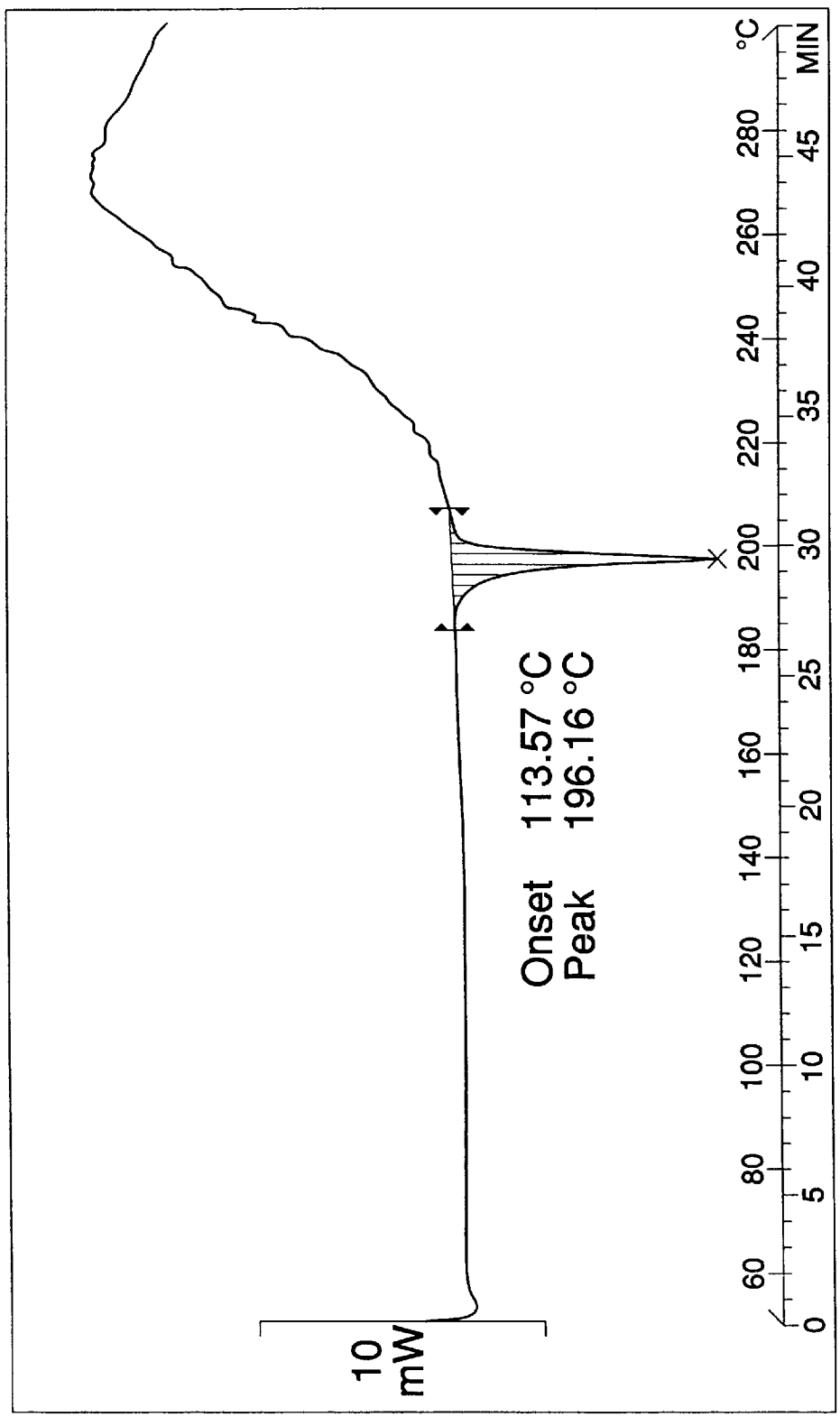
FIG. 2: Differential scanning calorimetry thermogram of crystalline anhydrous CP-472,295 measured on a Mettler Toledo Star® System. Vertical axis is mW; horizontal axis is temperature (° C.). The temperature was increased at a rate of about 5° C./min.
Figure 3:
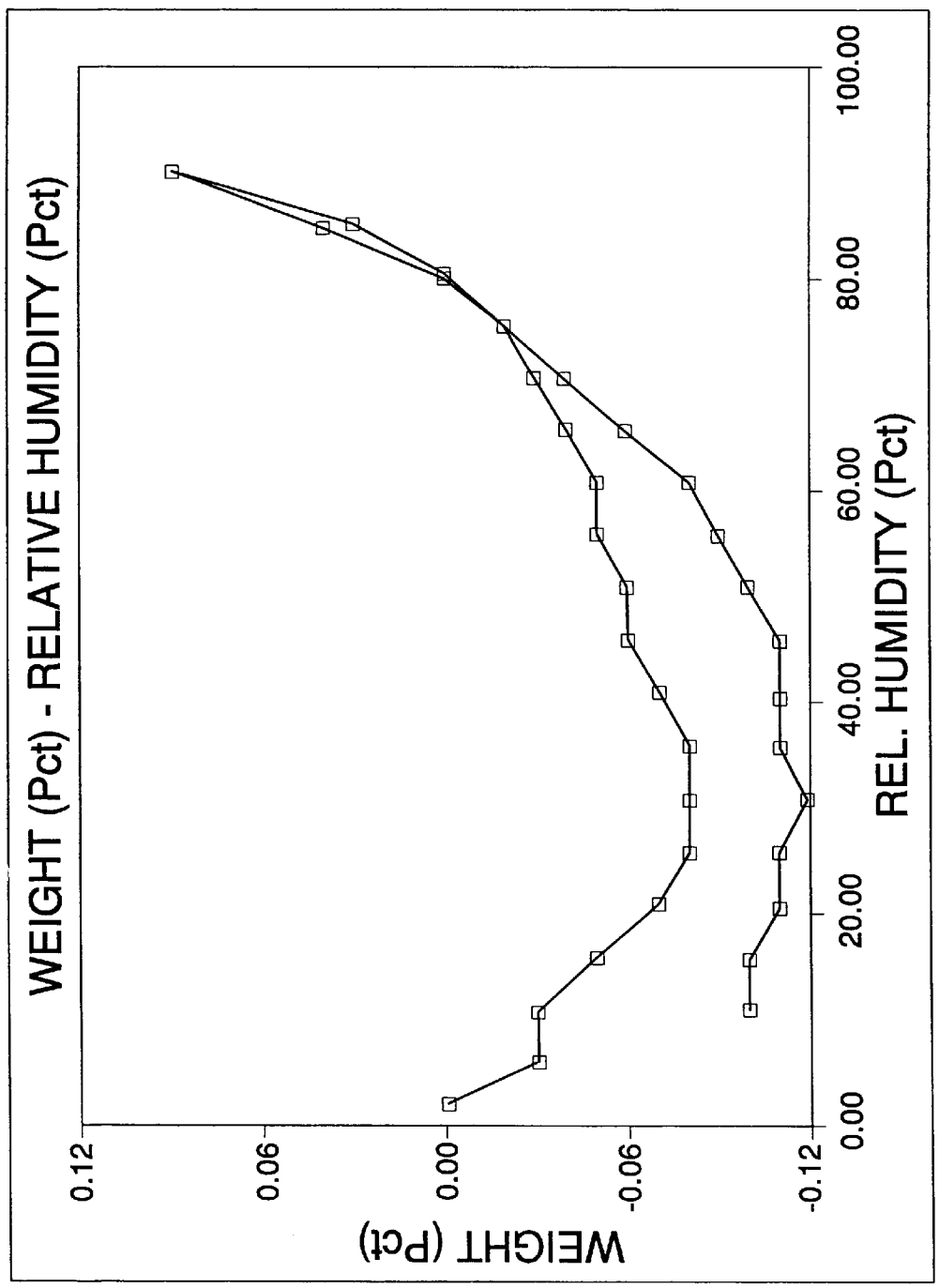
FIG. 3: Weight (Pct) - Relative humidity (Pct).

6. The crystalline form of claim 5 which has a differential scanning calorimetry spectrum according to FIG. 2.

7. A crystalline form of claim 1 which is non-hygroscopic for about 72 hours or to about 7 days when stored at about 87% relative humidity and 25° C.

8. A crystalline form of claim 1 which has an X-ray powder diffraction pattern that exhibits characteristic peaks expressed in 2θ at about 6.2, 7.6, 9.2, 9.5, 12.3, 12.9, 14.2, 14.6, 17.8, and 19.5.

Figure 4:
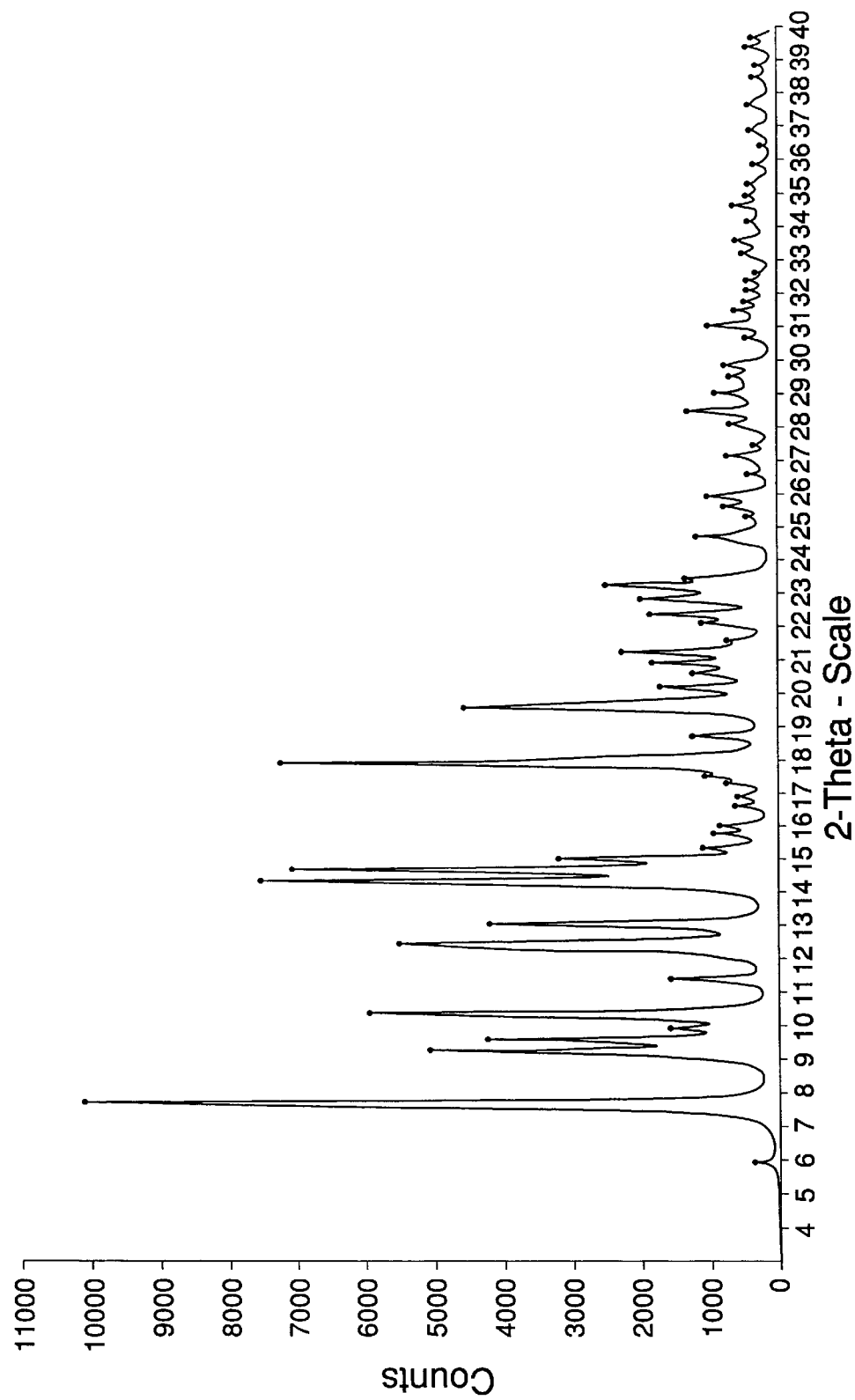
FIG. 4: X-ray powder diffraction pattern of crystalline CP-472,295 monohydrate. Vertical axis is intensity (CPS); horizontal axis is two theta (degrees).

9. The crystalline form of claim 8 which has an X-ray powder diffraction pattern according to FIG. 4.

10. A crystalline form of claim 1, which has the single crystal parameters that are provided in Table 1.

11. The crystalline form of claim 10 which comprises atoms at atomic positions relative to the origin of the unit cell as set forth in Table 2, bond lengths as set forth in Table 3, or bond angles as set forth in Table 4.

Figure 5:
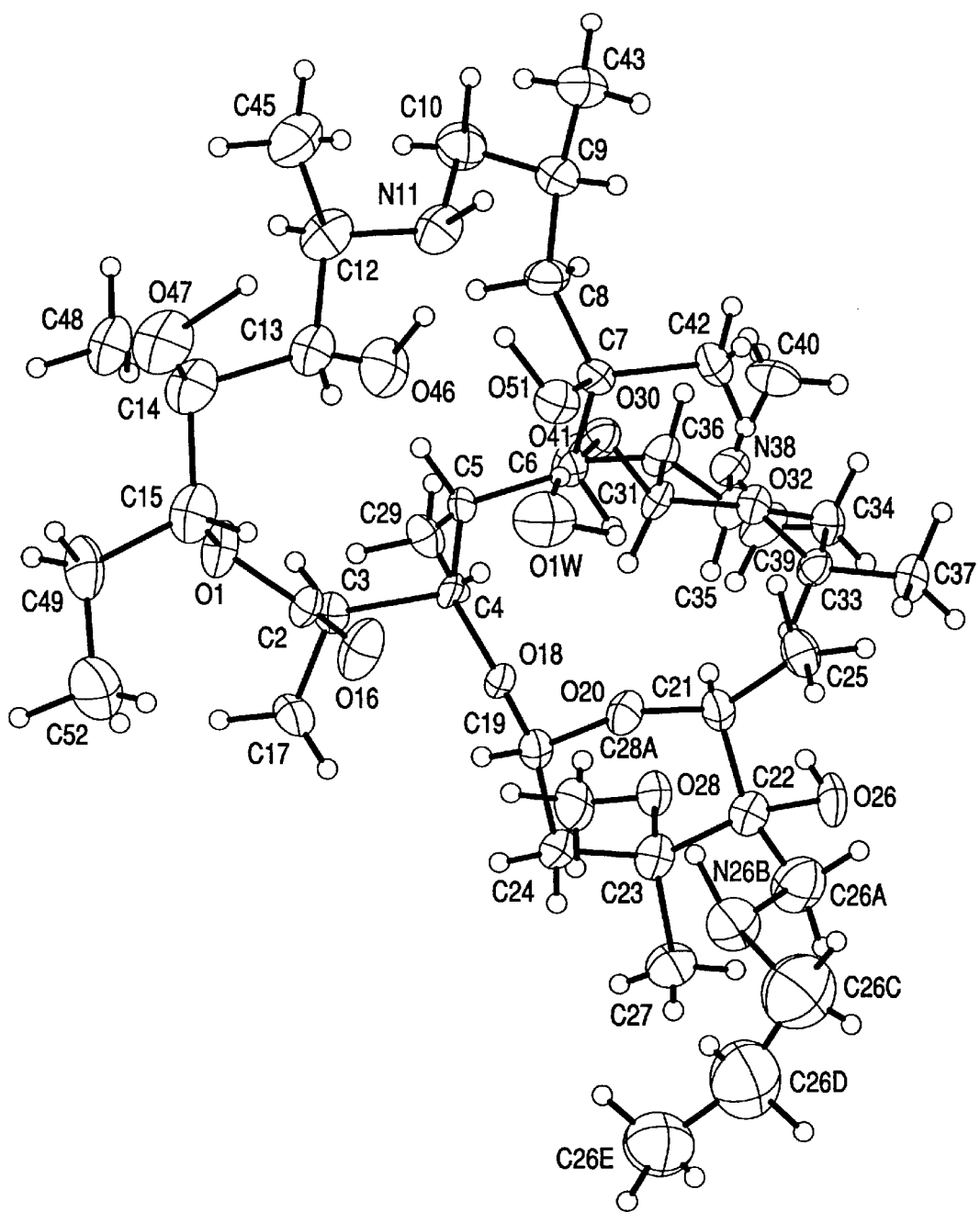
FIG. 5: Configuration of crystalline CP-472,295 monohydrate.

12. The crystalline form of claim 11 which has a single crystal structure according to FIG. 5.

Figure 6:
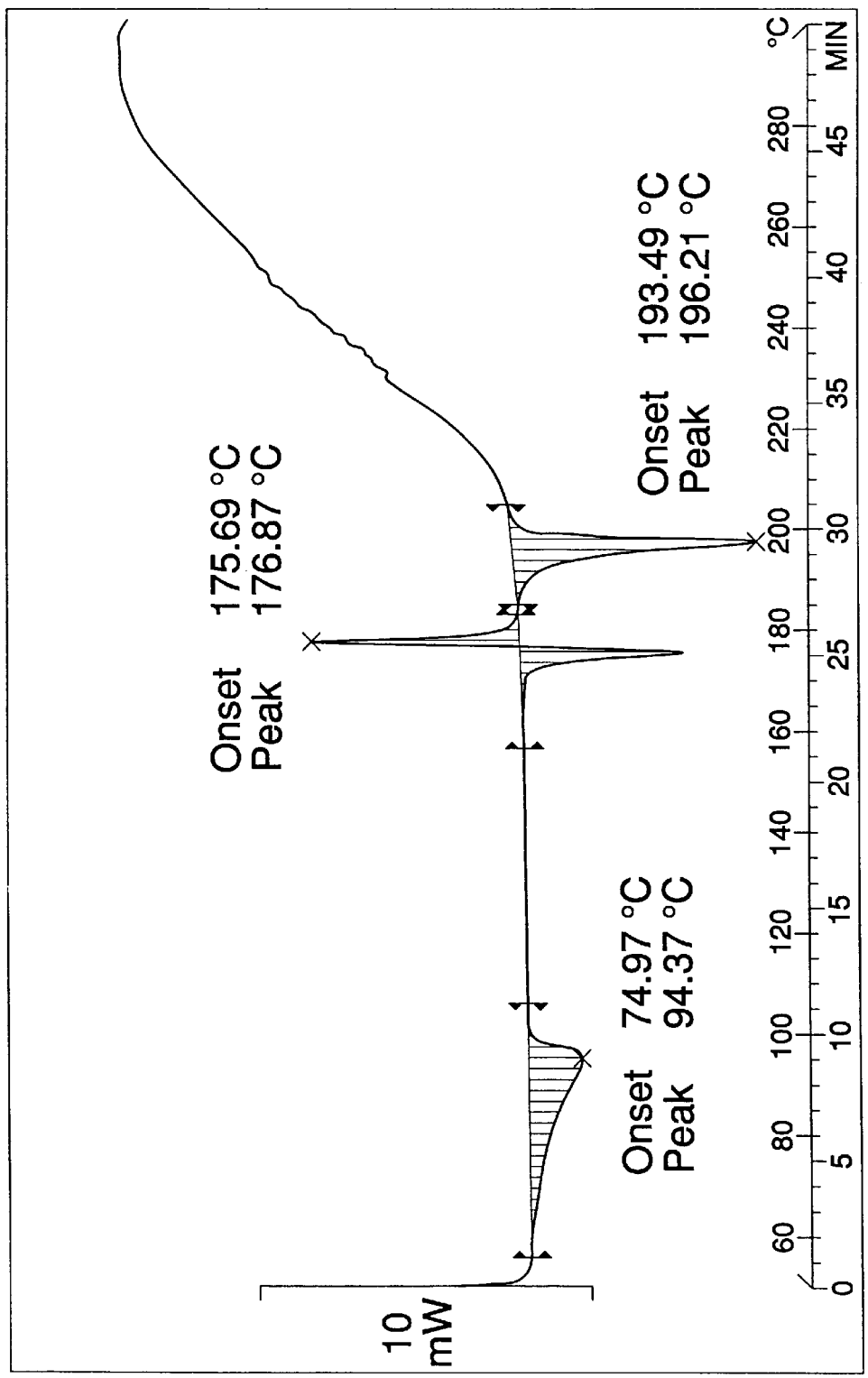
FIG. 6: Differential scanning calorimetry thermogram of crystalline CP-472,296 monohydrate, measured on a Mettler Toledo Star® System. Verical axis is mW; horizontal axis is temperature (° C.) with temperature being raised at a rate of about 5° C./min.

13. The crystalline form of claim 12 which has a differential scanning calorimetry spectrum according to FIG. 6.

14. A crystalline form of claim 1 which has an X-ray powder diffraction pattern which exhibits characteristic peaks expressed in 2θ at about 5.2, 7.4, 11.2, 11.7, 12.3, 12.9, 14.9, 15.4, 16.7, and 17.9.

Figure 7:
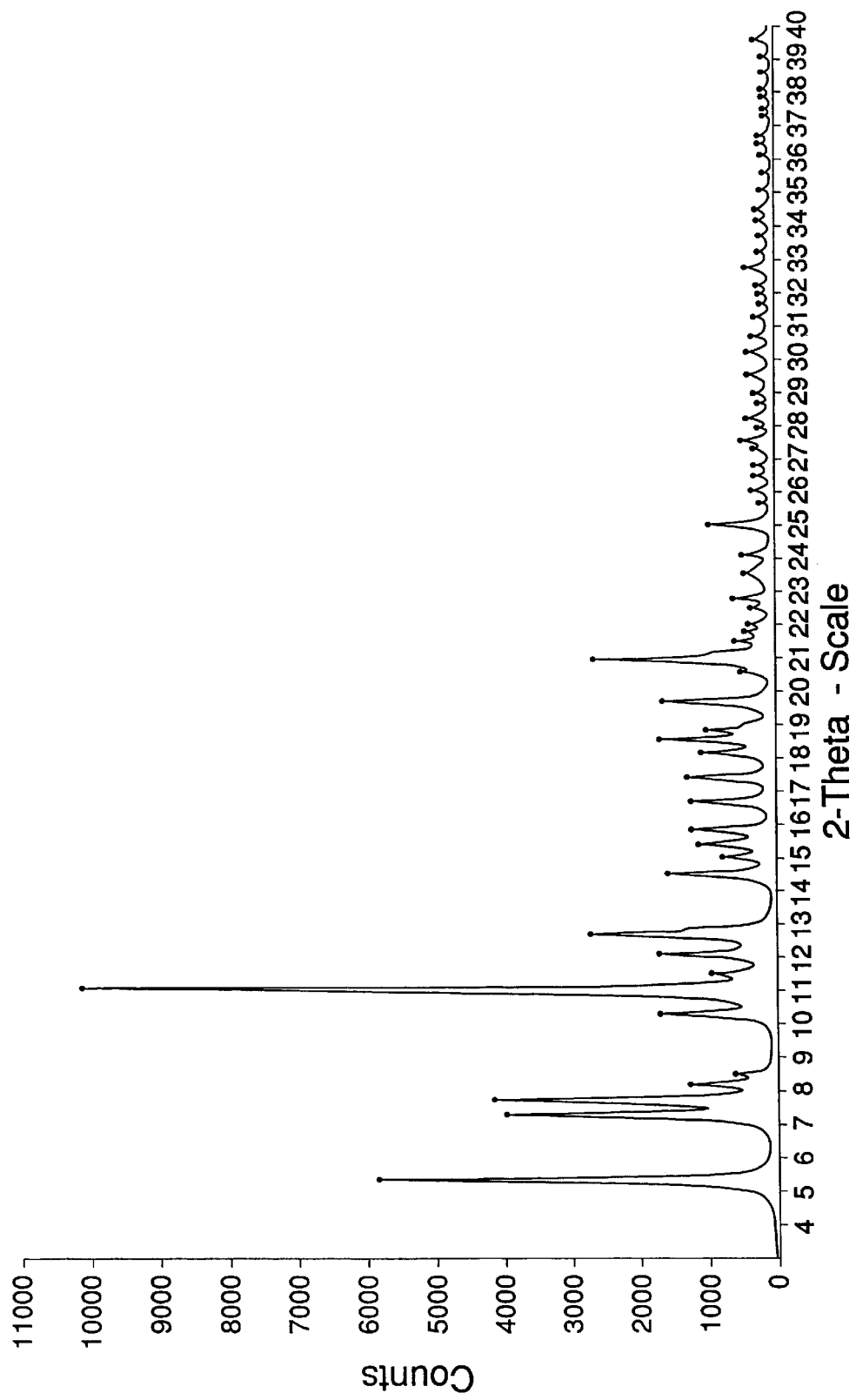
FIG. 7: Calculated X-ray powder diffraction pattern of crystalline CP-472,295 sesquahydrate. Vertical axis is intensity (CPS); horizontal axis is two theta (degrees).

15. The crystalline form of claim 14 which has an X-ray powder diffraction pattern according to FIG. 7.

16. A crystalline form of claim 1 which has a differential scanning calorimetry spectrum comprising an event with an onset at about 101° C.

Figure 8:
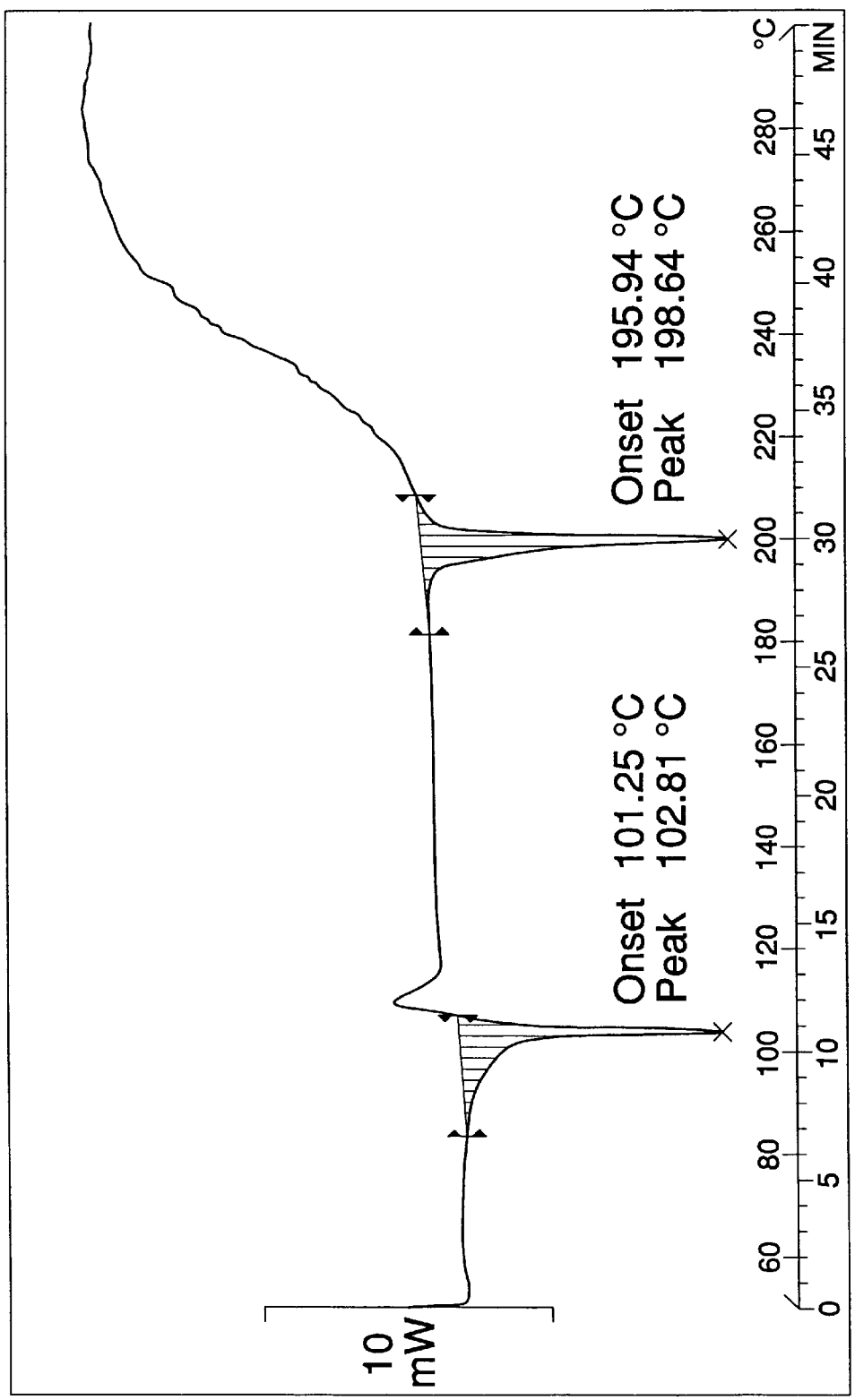
FIG. 8: Differential scanning calorimetry thermogram of a crystalline CP-472,295 sesquahydrate. This was measured on a Mettler Toledo Star® System. Vertical axis is mW; horizontal axis is temperature (° C.). The temperature was increased at a rate of about 5° C./min.

17. The crystalline form of claim 16 which has a differential scanning calorimetry spectrum according to FIG. 8.

18. A pharmaceutical composition comprising a crystalline form of a compound of Formula 1 and a pharmaceutically acceptable carrier.

19. The pharmaceutical composition of claim 18 wherein the crystalline form is one of anhydrous, monohydrate and sesquahydrate.

20. The pharmaceutical composition of claim 18 wherein said pharmaceutical composition is suitable for oral, rectal, intravenous parenteral, intramuscular parenteral, transdermal, buccal, nasal, sublingual, or subcutaneous administration.

* * * * *